US005312366A

United States Patent [19]

Vailancourt

[11] Patent Number: 5,312,366

[45] Date of Patent: May 17, 1994

[54] SHIELDED CANNULA ASSEMBLY

[76] Inventor: Vincent L. Vailancourt, 14 Bunyan Dr., Livingston, N.J.

[21] Appl. No.: 25,887

[22] Filed: Mar. 3, 1993

Related U.S. Application Data

[63] Continuation-in-part of Ser. No. 976,464, Nov. 16, 1992.

[51] Int. Cl.$^5$ ........ A61M 5/32

[52] U.S. Cl. ........ 604/192; 604/198

[58] Field of Search ........ 604/198, 192, 187, 110, 604/263

[56] References Cited

U.S. PATENT DOCUMENTS 3,134,380 5/1964 Armao ........ 604/198
4,449,539 5/1984 Sarstedt ........ 128/764
4,564,054 1/1986 Gustausson ........ 604/198 X
4,629,453 12/1986 Cooper ........ 604/192
4,695,274 9/1987 Fox ........ 604/198
4,725,267 2/1988 Vaillancourt ........ 604/263 X
4,735,618 4/1988 Hagen ........ 604/110 X
5,122,123 6/1992 Vaillancourt ........ 604/192

*Primary Examiner*—John D. Yasko
*Attorney, Agent, or Firm*—Francis C. Hand

[57] ABSTRACT

The shielded cannula assembly includes a tubular shield of latex rubber which is mounted over the cannula of the assembly. The shield includes a resilient collapsible tubular portion which is able to collapse in an accordion-like manner when a longitudinal force is imposed thereon. The shield also has a cap at the distal end which seals off a chamber in which the cannula is contained in a sterile manner. The cap includes a transverse wall which may be pierced by the cannula when the cannula is passed into a vial of medication or into a connector of an administration set.

14 Claims, 4 Drawing Sheets

SHIELDED CANNULA ASSEMBLY

This is a continuation-in-part of application Ser. No. 07/976,464 filed Nov. 16, 1992.

This invention relates to a shielded cannula assembly.

As is known, one major problem with a hypodermic needle as well as other needles is the threat of cutting oneself or another thereby exposing a blood vessel to the environment. This has become especially important in a hospital atmosphere where AIDS patients or AIDS members of the staff can infect others by having their blood interact, for example, by touching another person.

Various techniques have been forwarded to overcome this problem. These techniques include placing a shield over the needle after use; allowing for only a one time use of the needle with an automatic covering system which prevents further use, and various types of means for remotely shielding the needle after use. However, in none of these cases does the needle remain totally protected during an entire procedure. Further, if the needle is used twice, there is no provision to handle more than one use of the needle.

In practice, needles are almost always used at least twice. That is, in a first use of a needle which is attached to a syringe (a majority of the needle usage), the needle is used to puncture a drug vial and, if already constituted, draw the drug (or other medication) into the syringe. If the drug has not been reconstituted, for example, being in a powder state, then the needle must be used to reconstitute the drug. Once the syringe has been filled with medication and is otherwise ready for use on a patient, the needle of the syringe is used to pierce a septum on an I.V. Administration Set or to alternately puncture the body of the patient directly. This is followed by the administration of the drug. The needle is then withdrawn and the exposed needle is, in some fashion, shielded and ultimately discarded.

It has also been known, for example from U.S. Pat. Nos. 5,122,123 and 4,449,539 to mount a hollow needle within a female connector of a connector assembly in a recessed manner so as to prevent sticking. In addition, it has been known to mount a collapsible tube within the female connector about the hollow needle with a membrane at one end in order to form a sealed chamber to maintain the hollow needle in a sterile condition. When a male connector is inserted into the female connector, the tube is to be collapsed with the hollow needle piercing through the membrane.

Other techniques have also been employed for protecting against accidental sticking. For example, U.S. Pat. No. 4,725,267 describes the use of a post-injection needle sheath which can mounted on a needle hub to enclose a needle. U.S. Pat. No. 3,134,380 describes the use of a collapsible tubular shield on a needle hub with an absorbent pad at one end through which a needle may project when put into use.

U.S. Pat. No. 4,564,054 describes a relatively complex structure which mounts an apertured plate in front of a needle on a pair of side walls which collapse when the needle is passed through the plate.

U.S. Pat. No. 4,695,274 describes a protected hypodermic needle in which a removable safety jacket is placed about the needle of a syringe.

U.S. Pat. No. 4,735,618 describes a protective enclosure for a hypodermic syringe wherein the enclosure in which a needle guard disposed over the tip end of a needle is connected by a pair of collapsible arms to a sleeve which is mounted on the syringe.

U.S. Pat. No. 4,629,453 describes a tubular body which can be removably mounted over a needle projecting from a hub of a syringe.

In many of the above embodiments, the enclosure which is to protect against sticking leaves the needle exposed to the outside environment. As a result, the needle is not contained in a sterile condition.

Accordingly, it is an object of the invention to provide a cannula of an assembly with a continuous type of protection.

It is another object of the invention to render a hypodermic needle "stickless".

It is another object of the invention to provide a relatively simple structure for maintaining a cannula, such as a hypodermic needle in a closed system during use and when not in use.

It is another object of the invention to avoid contamination of the contents of a medicant or fluid containing vial, canister, bottle or the like due to repeated withdrawal of its contents via hypodermic needles and the like.

It is another object of the invention to provide a relatively simple structure to secure a hypodermic needle in a shielded condition from one use to another use as well as in between uses.

Briefly, the invention provides a shielded cannula assembly which comprises a housing, a hollow cannula mounted in and extending from the housing and a tubular shield extending from the housing about the cannula.

The housing is constructed in any suitable manner. For example, the housing may be in the form of a female luer hub for fitting on a syringe or other container which defines a chamber, for example, for receiving medications, fluids and the like. The housing may itself define a chamber to receive fluids. The hollow cannula which may be in the form of a hypodermic needle has a lumen which is in communication with the chamber of the housing in order to conduct the medication or fluid into or from the chamber as the case may be.

In accordance with the invention, the tubular shield which is exposed to the environment has a resilient longitudinally collapsible tubular portion concentrically about the cannula and a transverse wall at a distal end to form a sealed chamber with the tubular portion so as to contain the cannula therein in a sterile condition. This wall is made of a material to permit penetration of the cannula therethrough in response to longitudinal collapsing of the tubular portion. The material is also such as to reseal in response to expansion of the tubular portion and withdrawal of the cannula from the wall.

The tubular shield can be made so that the tubular portion and wall are integral. For example, the shield may be formed from a one-piece body made of an elastomeric material such a latex rubber.

The distal wall of the tubular shield is formed so as to have a flat face, for example, for abutting a septum of a vial containing a fluid. In this case, the face of the shield can be brought up against the septum of the vial and thereafter the cannula injected through the wall and septum into the interior of the vial for withdrawing fluid or medication therefrom. Upon removal from the vial, the tubular portion of the shield expands resiliently back to the normal condition so that the transverse wall again forms a sealed chamber relative to the cannula. In this way, the cannula is maintained in a closed system at all times. Furthermore, by maintaining the cannula in a closed system, that is, in a sterile condition, no contamination is introduced into the vial. Thus, contamination of the contents of the medicant or fluid containing vial is avoided even after repeated withdrawal of the contents of the vial using one or more cannulae of this type.

The tubular shield is constructed so as to allow the tubular portion to readily collapse when a longitudinal force is imposed upon the flat face of the transverse wall. In addition, the transverse wall is made part of a rigid cap which forms the end of the shield. Such a rigid cap serves to protect against the inadvertent passage of the free distal end of a hypodermic needle therethrough. That is, the rigid cap serves to protect against inadvertent passage of a sharp end of a needle through a side wall during transportation from place to place. In this respect, the cap can be made with an outside diameter greater than the outside diameter of the tubular portion.

In one embodiment, the transverse wall of the cap is sized of a thickness to permit penetration of the sharp end of a hypodermic needle therethrough in response to a longitudinal collapsing of the tubular portion of the shield while also permitting the resealing of the wall in response to expansion of the tubular portion and withdrawal of the needle therefrom.

In another embodiment, the transverse wall of the cap is provided with a slit to permit penetration of a non-cutting edge of a cannula such as a plastic or metal blunt cannula in response to a longitudinal collapsing of the tubular portion of the shield while also permitting the resealing of the wall in response to expansion of the tubular portion and withdrawal of the cannula therefrom.

The shielded hypodermic needle assembly may also be provided with restraining means for selectively preventing longitudinal collapsing or the tubular portion. For example, the means may be a rigid sleeve which is removably mounted about the tubular portion in order to prevent longitudinal collapsing of the tubular portion when not in use. The sleeve may also be longitudinally split so as to be readily fitted over the tubular portion when the cannula assembly is not in use.

In another embodiment, the restraining means may be in form of a sleeve which is rotatably mounted on the housing about the tubular shield. In this embodiment, the sleeve is provided with one or more longitudinal slots while the tubular shield itself is provided with one or more longitudinal ribs which can be aligned with the slot of the sleeve so as to permit longitudinal collapsing of the tubular shield. Thus, when the rib is not aligned with the slot, the tubular shield will not collapse. In an alternative embodiment, the sleeve may be provided with one or more internal grooves to receive the ribs of the tubular shield.

In still another embodiment, the restraining means may be in the form of at least one rigid elongated element which is pivotally mounted at one end on either the housing or the tubular shield for moving between a closed position concentric of the tubular shield to prevent collapsing thereof and an opened position spaced from the tubular shield to permit collapsing thereof. An extension tab may also be provided on the measured element to extend outwardly for manual gripping thereof in order to effect pivoting of the rigid element.

In still another embodiment, the restraining means may be in the form of a sleeve which is mounted on the housing for movement between an extended position abutting against a cap of a tubular shield and a retracted position spaced on the cap in order to permit collapsing of a tubular shield. Means may also be provided on the housing of the assembly for releasbly locking the sleeve in each of the two position.

In still another embodiment, the restraining means may be in the form of a cover which is removably mounted on the transverse wall of the tubular shield in order to prevent passage of the cannula through the wall. For example, the cover may be of disc shape to be slidably mounted over a cap of the tubular shield which defines the transverse wall.

The cannula assembly can be used in a generally conventional manner. In this respect, the restraining means, if present, is removed. The cannula can then be passed through the transverse wall of the shield into a drug vial to receive medication or connected to a connector of an administration set which is, in turn, connected to a patient in order to dispense medication. At this time, the tubular portion collapses in an accordion-like manner. When the cannula is withdrawn from the drug vial or administration set connector, the tubular portion springs back into an extended position so as to again completely encircle the cannula.

If the cannula assembly is to be transported from place to place, the restraining means is again placed over the tubular portion to maintain a positively locked condition which prevents the tubular portion from collapsing in an accordion-like manner.

The cannula assembly is otherwise of conventional construction, for example, employing a syringe which defines the housing in which the hollow cannula is mounted.

Further, the tubular shield may be constructed in a manner so as to be retrofitted onto existing syringes or made separately from a syringe.

These and other objects and advantages of the invention will become more apparent from the following detailed description taken in conjunction with the accompanying drawings wherein.

Figure 1:
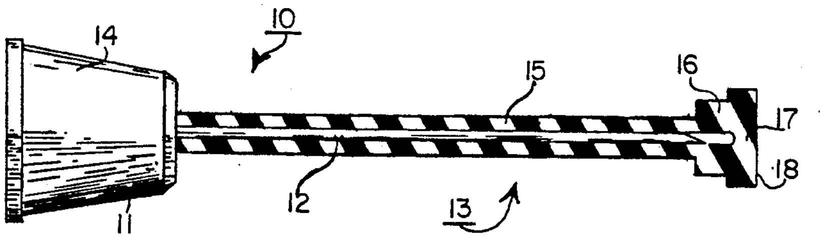
FIG. 1 illustrates a part cross-sectional view of a shielded hypodermic needle assembly in accordance with the invention.
Figure 3:
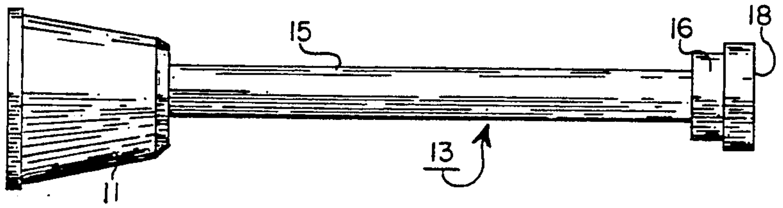
FIG. 3 illustrates the tubular shield in an extended position corresponding with FIG. 1.

Referring to FIGS. 1 and 3, the shielded cannula assembly 10 includes a housing 11, a cannula in the form of a hollow hypodermic needle 12 mounted in and extending from the housing 11 in conventional manner and a tubular shield 13 extending from the housing 11 concentrically about the needle 12.

The housing 11 is formed, for example, as a female luer hub with a chamber 14 which may be connected to a syringe (not shown) having a suitable chamber for receiving medications, fluids and the like.

The hypodermic needle 12 has a proximal end which is in communication with the chamber 14 in order to conduct the medication or fluid to and from the chamber 14 as is known.

The tubular shield 13 is exposed to the environment and is formed with a resilient longitudinal collapsible portion 15 and a cap 16 at the distal end of the tubular portion 15. As indicated, the tubular portion 15 is of constant outside diameter and is disposed concentrically about the allow needle 12 and is of relatively thin thickness to permit longitudinal collapsing while being relatively thicker than the outside diameter of the needle 12 to be protective. The cap 16 is relatively rigid relative to the collapsible tubular portion 15 and has an outside diameter greater than the outside diameter of the tubular portion. As shown in FIG. 1, the cap 16 has a T-shaped cross-section and is disposed over the tip of the needle 12. In addition, as indicated in FIG. 1, the cap 16 defines a transverse wall 17 at the distal end of the shield 13 in order to form a sealed chamber with the tubular portion 15 in order to contain the needle 12 therein in a sterile condition.

The transverse wall 17 is made of a thickness and of a material to permit penetration of the sharp end of the needle 12 therethrough in response to longitudinal collapsing of the tubular portion 15. The transverse wall 17 is also of a nature to reseal in response to withdrawal of the needle therefrom, for example, upon expansion of the tubular portion 15 into the condition illustrated in each of FIGS. 1 and 3.

Figure 2:
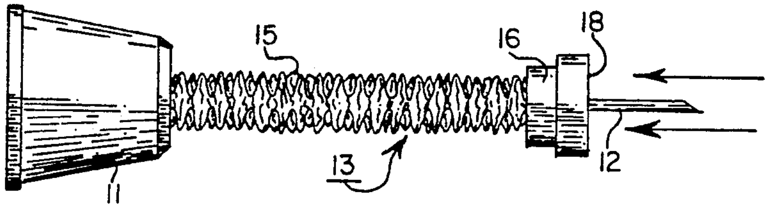
FIG. 2 illustrates a view of the assembly of FIG. 1 with the tubular shield in a partially collapsed state to expose a needle.

As shown in FIG. 2, when a longitudinal force F is imposed upon the cap 16, the tubular portion 15 collapses in an accordion-like manner so as to permit passage of the needle 12 through the transverse wall 17 of the cap 16. At the same time, the tubular portion 15 slides along the needle 12.

The transverse wall 17 of the cap 16 is formed to have a flat end face 18 for purposes as explained below. This flat free end face 18 of the tubular shield 13 may also be provided with a coating, such as a silver anti-microbial coating or other anti-microbial coating to render the surface free of micro-organisms. Alternatively, the cap 16 may be formed to have a silver anti-microbial powder therein. In this manner, sterile type connections may be made without recourse to wiping the surfaces with a suitable antiseptic, such as pividone-iodine prior to use of the assembly.

As indicated in FIG. 1, the tubular portion 15 and cap 16 are integral, that is, made of one piece. Further, the tubular shield 13 may be made of any suitable material, such as latex rubber, to impart resiliency to the tubular portion 15 so as to permit collapsing into a collapsed condition as shown in FIG. 2 and springing back into an extended position as illustrated in FIG. 3. In addition, the material should be such as to permit the needle 12 to pierce through the transverse wall 17 while also permitting the wall 17 to reseal upon withdrawal 12.

Figure 4:
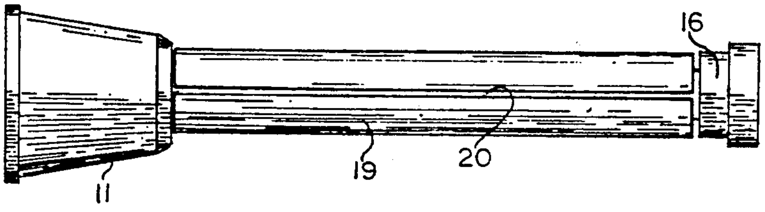
FIG. 4 illustrates a view similar to FIG. 3 of a hypodermic needle assembly employing a rigid sleeve about the tubular portion in accordance with the invention.
Figure 5:
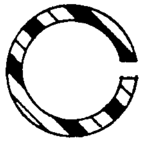
FIG. 5 illustrates a cross-sectional view of the rigid sleeve of FIG. 4.

Referring to FIGS. 4 and 5, the needle assembly 10 may also be provided with restraining means for selectively preventing longitudinal collapsing of the tubular portion 15. This means may be in the form of a rigid sleeve 19 which serves to prevent longitudinal collapsing of the tubular portion 15 of the shield 13 when not desired. For example, the rigid sleeve 19 is provided with a longitudinal split 20 so as to be removably mounted about the tubular portion 15.

Figure 6:
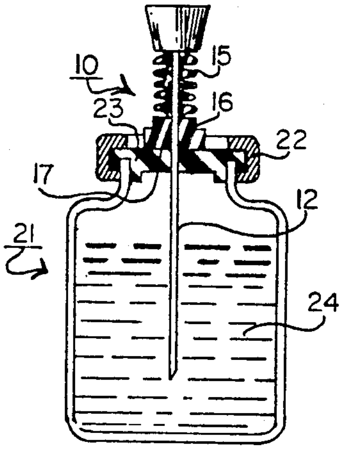
FIG. 6 illustrates a cross-sectional view of the shielded hypodermic needle assembly during introduction into a vial of medication.

Referring to FIG. 6, hypodermic needle assembly may be utilized to withdraw a fluid such as an anesthetic from a vial 21 while maintaining a sterile condition not only of the needle 12 but also of the contents of the vial 21. For example, the vial 21 may be provided with a cap 22 having a septum 23 across an opening thereof. Typically, the cap 22 would be sealed in hermetic manner relative to the vial 21 so as to maintain a contents 24 of the vial in a sterile condition.

When it is desired to remove some of the contents 24 from the vial 21, the needle assembly 10 is brought into abutment with the septum 23 so that the flat face 18 of the cap 16 is in face to face contact with the septum 23. At this time, if the cap 16 has not been provided with an anti-microbial coating, the face 18 of the cap 16 may be wiped with a suitable antiseptic along with the face of the septum 23.

Next, the needle 12 is pushed into the vial 21 so that the needle 12 passes through the transverse wall 17 of the shield 13 and the septum 23 of the vial 21. During this time, the relatively rigid block-like cap 16 provides a relatively large end face 18 which can be seated against the septum 23 of the vial 21 so that an effective seal can be maintained between the cap 16 and septum 23 during penetration of the needle 12 through the septum 23 under the spring-like force generated by the collapsed tubular portion 15. After withdrawal of the antiseptic, the needle 12 can be withdrawn from the vial 21. At this time, the tubular portion 15 of the shield 13 springs back so that the transverse wall 17 again seals the chamber containing the needle 12. Thus, the needle 12 is maintained in a closed system at all times.

Since the needle 12 is not exposed to atmosphere there is little risk of contamination of the needle 12. Thus, the needle 13 can be reinserted into the vial 21 time and time again without risk of carrying contaminants into the contents 24 of the vial 21.

The tubular shield 13 can be readily made of any suitable material. However, latex rubber is preferred. Further, the transverse wall 17 of the cap 16 may be pre-slit in order to facilitate passage of the hollow needle 12 therethrough.

Figure 7:
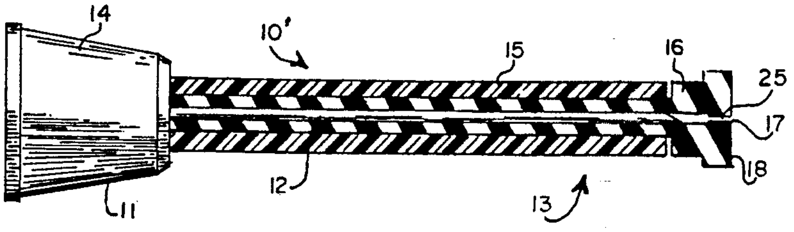
FIG. 7 illustrates a part cross-sectional view of a shielded cannula assembly employing a blunt cannula in accordance with the invention.

Referring to FIG. 7, wherein like reference characters indicate like parts as above, the shielded cannula assembly 10′ is formed with a blunt ended cannula 12′ of plastic or metal. In addition, the transverse wall 17 of the cap 16 is provided with a slit 25 in order to facilitate passage of the blunt end of the cannula 12′therethrough. In order respects, the assembly 10′ functions and is used in the same manner as the embodiment described above with respect to FIGS. 1 to 5.

Figure 8:
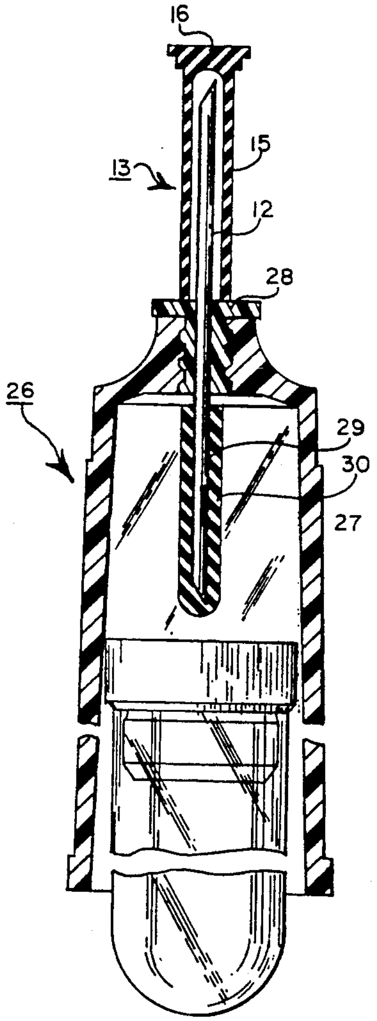
FIG. 8 illustrates a cross-sectional view of a further embodiment of a shielded assembly in accordance with the invention.

Referring to FIG. 8, wherein like reference characters indicate like parts as above, the cannula assembly 26 may be constructed, for example, for use in collecting blood. As shown, the assembly includes a housing 27 of cup shape, a hub 28 which is integral with the housing 27, a hollow cannula 12, as above, which extends from one end of the hub 28 and a second cannula 29 which extends from an opposite end of the hub 28 in a recessed manner within the housing 27. In addition, a tubular shield 13 is disposed about the cannula 12 while a one-way rubber valve 30 is mounted on the hub 28 and disposed about the second cannula 29 within the housing 27. This valve 30 may be constructed in the same fashion as the tubular shield 13 or may be constructed simply as a sleeve which is able to collapse about the cannula 29 while permitting the cannula 29 to pass therethrough.

Figure 9:
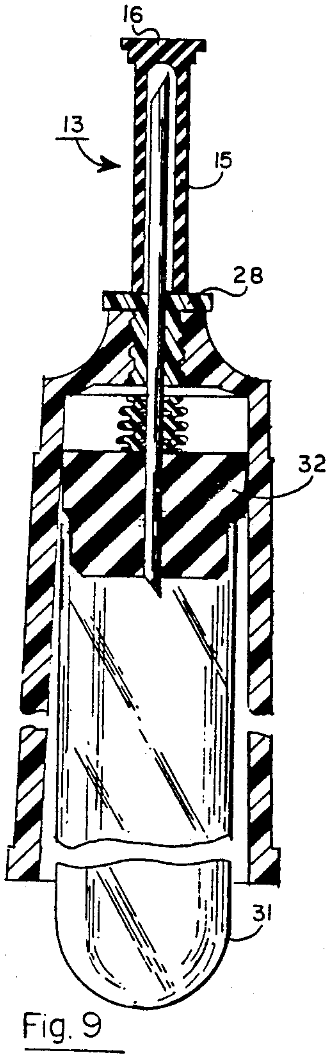
FIG. 9 illustrates a the shielded assembly of FIG. 8 in use with a blood collecting tube.

The assembly 26 may be used, for example, as shown in FIG. 9 with a blood collecting tube to collect blood from a patient. As indicated, the blood collecting tube 31 is of conventional structure having a rubber stopper 32 or the like at one end to seal the contents of the tube 31. In addition, the tube is under vacuum.

When in use, the housing 27 of the assembly is fitted over the end of the blood collecting tube 31 and the cannula 29, such as a sharp ended needle, is pierced through the stopper 32 into the interior of the tube 31. At this time, the one-way rubber valve 30 collapses in an accordion-like manner to maintain a seal between the stopper 32 and hub 28 so that the vacuum is maintained through the cannula 29. Thereafter, the cannula 12 can then be connected to a suitable connector which, in turn, is connected to a vein of a patient to permit blood to be withdrawn under the vacuum pressure into the tube 31. Alternatively, the cannula 12 may communicate with the vein of a patient in other manners. In any event, during this time, the tubular portion 15 of the shield 13 would collapse while the cannula 12 is passed through the cap 16.

Figure 10:
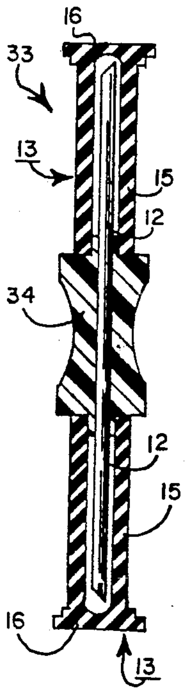
FIG. 10 illustrates a transfer needle embodiment in accordance with the invention.

Referring to FIG. 10, the shielded assembly may be used as a transfer needle assembly 33. In this respect, a pair of cannulae 12 are mounted at opposite ends of a common housing 34 with the lumen of the cannulae 12 in communication. In addition, a shield 13 is mounted over each cannulae 12 and is mounted on the housing 34 in any suitable manner. Such a transfer needle 33 may be used, for example, for transferring fluid from one container to another container, for example, from one vial to another vial.

Figure 11:
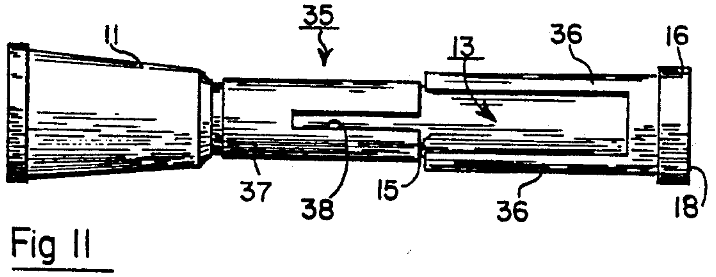
FIG. 11 illustrates a side view of a modified shielded assembly using a modified restraining means employing a rotatable sleeve.
Figure 13:
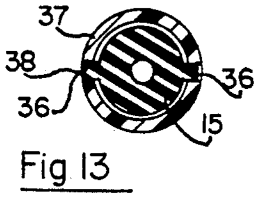
FIG. 13 illustrates a cross-sectional view taken on line 13—13 of FIG. 12.
Figure 12:
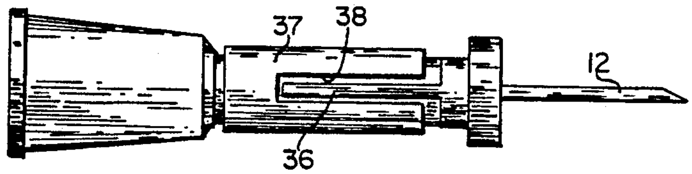
FIG. 12 illustrates a view of the assembly of FIG. 11 with the rotatable sleeve in a release position.

Referring to FIGS. 11 to 13, wherein like reference characters indicate like parts as above, the shielded assembly 35 includes a restraining means for selectively preventing longitudinal collapsing of the tubular portion 15 of the tubular shield 13. In this respect, the restraining means employs a plurality of longitudinal ribs 36 which are integrally formed on the collapsible portion 15. As indicated, the ribs 36 extend from the cap 16 towards the housing 11. In addition, the restraining means employs a sleeve 37 which is rotatably mounted on the housing 11 or, as illustrated, about the tubular shield 13 to abut against the housing 11. This sleeve 37 has a plurality of longitudinal slots conforming in number to the number of ribs 36 on the tubular shield 13. The ribs 36 and slots 38 relative to each other so that the ribs 36 may slide into the slots 38 during collapsing of the resilient collapsible portion 15 of the shield 13.

As illustrated in FIG. 11, the sleeve 37 is in a position such that the ribs 36 and slots 38 are non-aligned. Hence, the ribs 36 would abut against the end wall of the sleeve 37 should one attempt to collapse the portion 15 of the shield 13.

As illustrated in FIG. 12, when the sleeve 37 is rotated relative to the shield 13 so that the ribs 36 and slots 38 are aligned, the portion 15 of the shield 13 can be collapsed so that the hypodermic needle 12 can be exposed for use.

Figure 14:
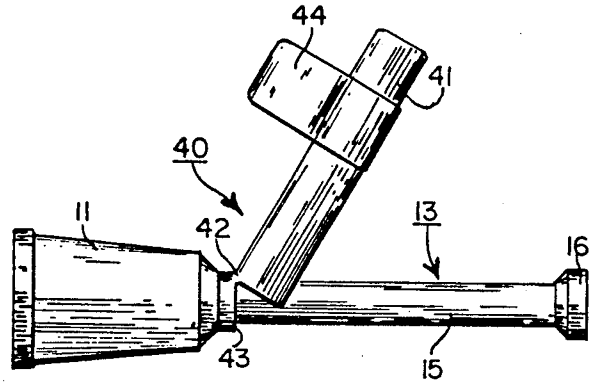
FIG. 14 illustrates a view of a further modified retraining means in accordance with the invention.
Figure 15:
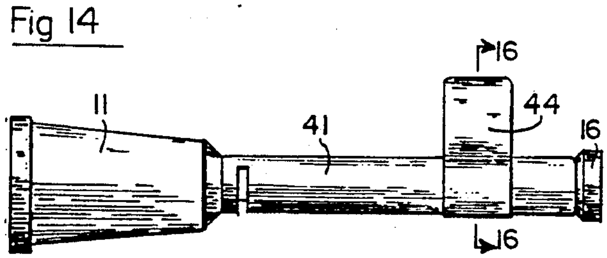
FIG. 15 illustrates a view of an assembly as shown in FIG. 14 with the restraining means in a locking position.
Figure 16:
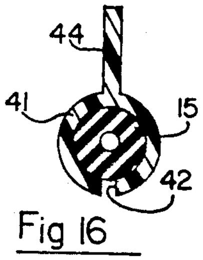
FIG. 16 illustrates a cross-sectional view taken on line 16—16 of FIG. 15.

Referring to FIGS. 14 to 16, wherein like reference characters indicate like parts as above, the shielded assembly 40 employs a restraining means in the form of a rigid elongated element 41 which is pivotally mounted at one end on either the housing 11 or on the tubular shield 15 for moving between a closed position concentric of the tubular shield 15 (see FIG. 15) to prevent collapsing thereof and an opened position spaced from the tubular shield 15 (see FIG. 14) to permit collapsing of the tubular shield 15 in a manner as described above with respect to FIG. 2. As indicated in FIG. 16, the rigid element 41 is in the form of a split sleeve to defined a longitudinal slot 42. During movement of the element 41 from the opened position (FIG. 14) to the closed position (FIG. 15) the element 41 expands radially so as to fit about the tubular shield 15.

As indicated in FIG. 14, the rigid element 41 is connected by a hinge 42 to a collar 43 which can be slidably mounted over the tubular shield 15 of fixably secured to the hub 11.

Referring to FIG. 15, when in the closed position the rigid element 41 abuts against the cap 16 of the shield 13 so as to prevent collapsing of the tubular portion 15.

As indicated in FIGS. 14 to 16, an extension tab 44 extends outwardly of the rigid element 41 to permit manual gripping thereof in order to facilitate pivoting of the element 41 between the opened and closed positions thereof. This tab 44 may be integral with the element 41. As indicated in FIG. 16, the extension tab 44 at element 41 may be made of a suitable plastic material to provide a sufficiently stiff resistance to longitudinal collapsing while permitting flexation to fit about the tubular portion 15.

Figure 17:
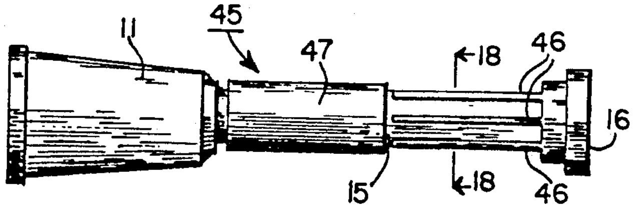
FIG. 17 illustrates a view of an assembly having a further modified restraining means in accordance with the invention.
Figure 18:
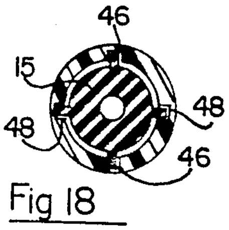
FIG. 18 illustrates a view taken on line 18—18 of FIG. 17.

Referring to FIGS. 17 and 18, wherein like reference characters indicate like parts as above, the shielded assembly 45 employs a restraining means which includes a plurality of longitudinal ribs 46 on the tubular shield 15 and a sleeve 47 which is rotatable about the shield 15. In this respect, the ribs 46 and sleeve 47 are similar to the ribs 36 and sleeve 37 of FIGS. 11 to 13. However, the sleeve 47 is provided with a plurality of longitudinally disposed internal grooves 48 (see FIG. 18) for selectively receiving the ribs 46. As above, the sleeve 47 can be rotated into a position to prevent longitudinal collapsing of the tubular portion 15 by non-alignment of the ribs 46 with the grooves 48. When the sleeve 47 is rotated into a position in which the ribs 46 and grooves 48 are in alignment, the tubular portion 15 can be collapsed.

Figure 19:
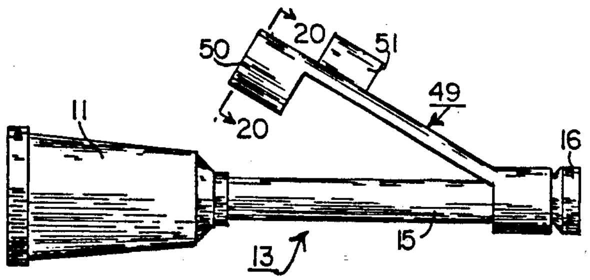
FIG. 19 illustrates a view of a further modified restraining means in accordance with the invention.
Figure 20:
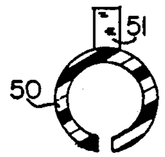
FIG. 20 illustrates a view taken on line 20—20 of FIG. 19.

Referring to FIGS. 19 and 20, wherein like reference characters indicate like parts as above, the restraining means is in the form of a one piece rigid elongated element 49 having an arcuate cross-sectional shape which is a minor fraction of a circle. In addition, the element 49 is pivotally connected to the cap 16 of the shield 13 for pivoting between an opened position as shown in FIG. 19 and a closed position (not shown). In addition, the element 49 carries an extension 50 at the free end which has an arcuate cross-sectional shape which is a major fraction of a circle. As indicated in FIG. 20, the extension 50 has a longitudinal slot which permits fitting of the extension 50 over the tubular portion 15 adjacent to the housing 11. When in a closed position, this extension 50 envelopes the tubular portion 13 so as to abut against the housing 11 and thereby prevent collapsing of the tubular portion 15.

As above, an extension tab 51 is formed on the element 49 to extend outwardly for manual gripping thereof in order to facilitate pivoting of the element 49 between the opened and closed positions thereof.

Figure 21:
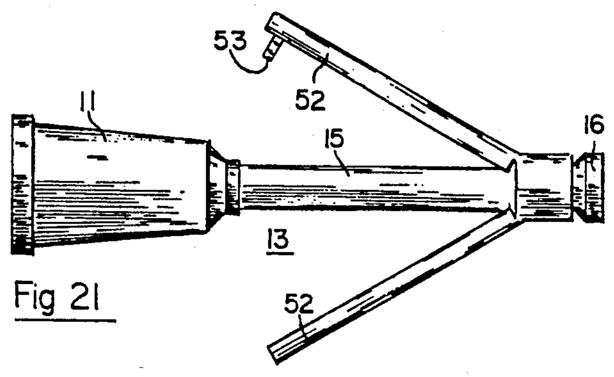
FIG. 21 illustrates a view of a restraining means employing a plurality of elongated elements of arcuate cross-section in accordance with the invention.

Referring to FIG. 21, wherein like reference characters indicate like parts as above, the restraining means may employ a pair of rigid elements 52 each of which is pivotally connected to the cap 16 of the tubular shield 13. In this case, each element 52 has a semi-circular shape cross-sectional so that when closed together, the two elements 52 completely enclose the tubular portion 15. In addition, a means in the form of a locking tab 53 may be formed on one of the elements 52 so as to engage about or in the other element 52 when both are moved into a closed position about the tubular shield 13.

Figure 22:
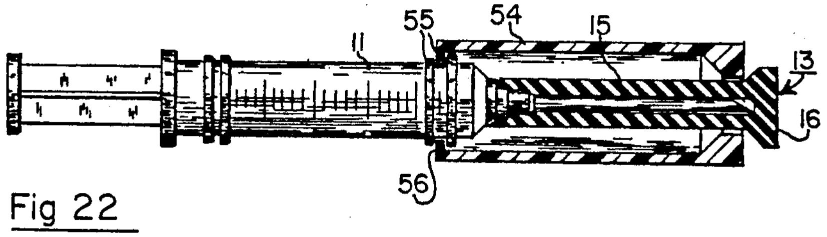
FIG. 22 illustrates a view of a further modified restraining means employing a sleeve in accordance with the invention.
Figure 23:
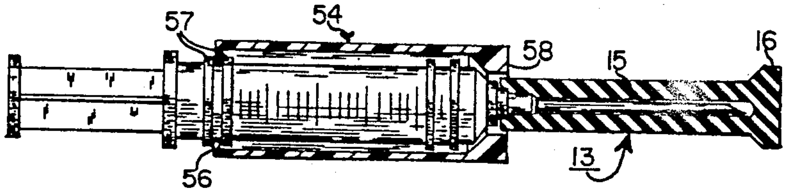
FIG. 23 illustrates a view similar to FIG. 2 of the sleeve in a retracted position.

Referring the FIGS. 22 and 23, wherein like reference characters indicate like parts as above, the restraining means may be in the form of a sleeve 54 which is slidably mounted on the housing 11 for movement between an extended position as shown in FIG. 22 abutting the cap 16 and a retracted position as shown in FIG. 23 spaced from the cap 16 to permit collapsing of the tubular shield 13. As indicated, the sleeve 54 is of plastic material and can be readily slid back and forth in a telescoping manner relative to the tubular portion 15 of the shield 13.

A locking means is also provided for releasably locking the sleeve 54 in each of the extended position and retracted position. As shown in FIG. 22, the locking means includes a pair of annular collars 55 on the housing 11 which define an annular recess which cooperates with a radially inward flange or lip 56 on the sleeve 54 so as to lock the sleeve 54 in the extended position. The sleeve 54 and lip 56 are sufficiently resilient so as to permit the sleeve 54 to be manually grasped and pulled rearwardly to allow collapsing of the tubular portion 15 of the shield 13.

As shown in FIG. 23, the locking means also includes a pair of annular collars 57 towards the rear of the housing 11 which define a recess therebetween to receive the lip 56 of the sleeve 54 in a releasable locking manner. The forward end of the sleeve 54 may also be shaped so as to form a radially inwardly directed flange 58 to abut against the housing 11.

Figure 24:
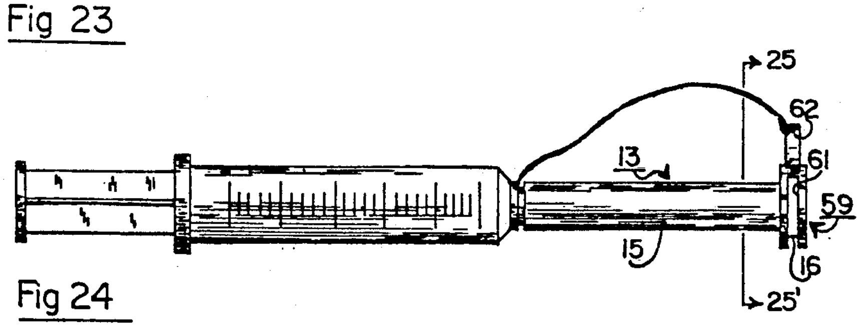
FIG. 24 illustrates a side view of an assembly having a modified restraining means in the form of a removable cover.
Figure 25:
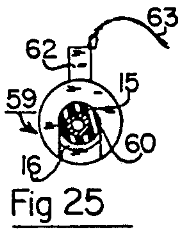
FIG. 25 illustrates a view taken on line 25—25 of FIG. 24.
Figure 26:
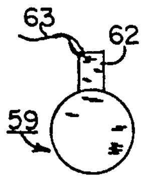
FIG. 26 illustrates a front view of the cover of FIG. 24 in accordance with the invention.

Referring to FIGS. 24 to 26 wherein like reference characters indicate like parts as above, the restraining means may be in form of a cover 59 which is removably mounted on the cap 16 of the shield 13 so as to prevent passage of the needle 12 through the transverse wall 17 of cap 16. In this respect, should the assembly be pressed against an object, the needle 12 will be blocked by the cover 59 from passing completely through the transverse wall 17. In this respect, the cover 59 may be made of any suitable material such as a rigid plastic.

As shown in FIGS. 25 and 26, the cover 59 is of disc shape. Also, as indicated in FIG. 25, the cover 59 has a U-shaped slot 60 at the rear so as to pass over over the tubular portion 15 of the shield 13. In addition, as shown in FIG. 24, the cover has slotted side walls 61 which communicate with the slot 60 to fit over the cap 16 in a slide fit relationship.

The cover 59 may also be provided with an outwardly extending tab 62 to facilitate manual grasping for manipulation of the cover 59 onto and from the cap 16. Still further, the tab 62 may connected by a tether 63 to the housing 11 or to proximal end of the tubular shield 15 (in a manner not shown).

The invention thus provides a cannula assembly which maintains a hollow cannula in a closed system at all times.

Further, the invention provides a shielded hypodermic needle assembly which is able to avoid contamination of the contents of a fluid containing vial or bottle due to repeated withdrawal of the contents of the vial using the hypodermic needle or needles.

Further, the invention provides a shielded cannula assembly which can be employed in various manners such as on a syringe to protect a hypodermic needle extending therefrom, in a blood collecting container, and a transfer needle assembly for transferring fluid, or gases, from one container or vial to another container or vial.

What is claimed is:

1. A shielded cannula assembly comprising a housing;

a hollow cannula mounted in and extended from said housing, said cannula having a lumen for passage of a fluid therethrough;

a tubular shield extending from said housing in an exposed manner relative to the surrounding environment, said shield having a resilient longitudinally collapsible tubular portion concentrically about said cannula and a transverse wall at a distal end to form a sealed chamber with said tubular portion to contain said cannula therein in a sterile condition, said wall being made of a material to permit penetration of said needle therethrough in response to longitudinal collapsing of said tubular portion and resealing of said wall in response to expansion of said tubular portion and withdrawal of said cannula therefrom; and means for selectively preventing longitudinal collapsing of said tubular portion.

2. A shielded cannula assembly as set forth in claim 1 wherein said tubular portion and said wall are integral.

3. A shielded cannula assembly as set forth in claim 2 wherein said shield is made of latex rubber.

4. A shielded cannula assembly as set forth in claim 1 wherein said wall has a flat end face for abutting a septum of a vial containing fluid.

5. A shielded hypodermic needle assembly as set forth in claim 1 wherein said tubular shield includes a plurality of longitudinal ribs and said means includes a sleeve rotatably mounted on said housing concentrically about said tubular shield, said sleeve having a plurality of longitudinal slots therein for selective alignment with said ribs of said tubular shield to permit longitudinal collapsing of said tubular shield.

6. A shielded hypodermic needle assembly as set forth in claim 1 wherein said cannula is a hypodermic needle and said housing has a chamber in communication with said lumen of said needle.

7. A shielded hypodermic needle assembly as set forth in claim 1 which further comprises an antimicrobial coating on a free end face of said wall.

8. A shielded hypodermic needle assembly comprising a housing defining a chamber;

a hollow hypodermic needle mounted in and extending from said housing, said needle having a lumen in communication with said chamber;

a one piece elastomeric shield extending from said housing in an exposed manner relative to the surrounding environment, said shield having a resilient longitudinally collapsible tubular portion concentrically about said needle and a cap defining a transverse wall at a distal end to form a sealed chamber with said tubular portion to contain said needle therein in a sterile condition; and means for selectively preventing longitudinally collapsing of said tubular portion.

9. A shielded hypodermic needle assembly as set forth in claim 8 wherein said cap is of rigid block-like shape and said wall has a flat end face for abutting a septum of a vial containing fluid.

10. A shielded hypodermic needle assembly as set forth in claim 8 wherein said tubular portion has a constant outside diameter and said cap has an outside diameter greater than said outside diameter of said tubular portion.

11. A shielded hypodermic needle assembly as set forth in claim 10 wherein said cap has a T-shaped cross-section.

12. A shielded hypodermic needle assembly as set forth in claim 8 which further comprises an antimicrobial coating on a free end face of said wall.

13. A shielded hypodermic needle assembly a housing defining a chamber;

a hollow hypodermic needle mounted in and extending from said housing, said needle having a lumen in communication with said chamber;

a one piece elastomeric shield extending from said housing, said shield having a resilient longitudinally collapsible tubular portion concentrically about said needle and an enlarged relatively rigid cap defining a transverse wall at a distal end, said wall being sized to permit penetration of said needle therethrough in response to longitudinal collapsing of said tubular portion and resealing of said wall in response to expansion of said tubular portion and withdrawal of said needle therefrom; and means removably mounted about said tubular portion for selectively preventing longitudinal collapsing of said tubular portion.

14. A shielded hypodermic needle assembly as set forth in claim 13 wherein said wall has a flat end face for abutting a septum of a vial containing fluid.

* * * * *

UNITED STATES PATENT AND TRADEMARK OFFICE

CERTIFICATE OF CORRECTION

PATENT NO. : 5,312,366

DATED : May 17 1994

INVENTOR(S) : VINCENT L. VAILLANCOURT

It is certified that error appears in the above-identified patent and that said Letters Patent is hereby corrected as shown below:

Column 5, line 58 "allow" should be -hollow-
Column 8, line 49 "defined" should be -define-
Line 56 "of" should be -or-
Column 12, after line 38 add the following claims:

15. A shielded hypodermic needle as set forth in claim 1 wherein said means includes a longitudinally split rigid sleeve removably mounted about said tubular portion.

16. A shielded hypodermic needle assembly as set forth in claim 1 wherein said tubular shield includes a plurality of longitudinal ribs and said means includes a sleeve rotatably mounted on said housing concentrically about said tubular shield, said sleeve having a plurality of longitudinal internal grooves therein for selective alignment with said ribs of said tubular shield to permit longitudinal collapsing of said tubular shield.

17. A shielded hypodermic needle assembly as set forth in claim 1 wherein said means includes at least one rigid elongated element pivotally mounted at one end on one of said housing and said tubular shield for moving between a closed position concentric of said tubular shield to prevent collapsing thereof and opened position spaced from said tubular shield to permit collapsing thereof.

18. A shielded hypodermic needle assembly as set forth in claim 17 wherein said means includes an extension tab extending outwardly of said rigid element for manual gripping thereof to effect pivoting of said element.

UNITED STATES PATENT AND TRADEMARK OFFICE
CERTIFICATE OF CORRECTION

PATENT NO. : 5,312,366

DATED : May 17, 1994

INVENTOR(S) : VINCENT L. VAILLANCOURT

It is certified that error appears in the above-identified patent and that said Letters Patent is hereby corrected as shown below:

19. A shielded hypodermic needle assembly as set forth in claim 17 wherein said elongated element is a slotted sleeve.

20. A shielded hypodermic needle assembly as set forth in claim 17 wherein said elongated element has an arcuate cross-section.

21. A shielded hypodermic needle assembly as set forth in claim 17 wherein said elongated element has an arcuate section at a free end for abutting the other of said housing and said tubular shield in said closed position.

22. A shielded hypodermic needle assembly as set forth in claim 1 wherein said tubular shield has a cap at one end forming said transverse wall and wherein said means includes a sleeve mounted on said housing for movement between an extended position abutting said cap and a retracted position spaced from said cap to permit collapsing of said tubular shield and locking means for releaseably locking said sleeve in each of said positions.

23. A shielded hypodermic needle assembly as set forth in claim 22 wherein said locking means includes an annular flange on said sleeve and a pair of longitudinally spaced apart annular recesses in said housing for selectively receiving said flange therein.

UNITED STATES PATENT AND TRADEMARK OFFICE
CERTIFICATE OF CORRECTION

PATENT NO. : 5,312,366 Page 3 of 3

DATED : May 17, 1994

INVENTOR(S) : VINCENT L.VAILLANCOURT

It is certified that error appears in the above-identified patent and that said Letters Patent is hereby corrected as shown below:

24. A shielded hypodermic needle assembly as set forth in claim 1 wherein said means includes a cover removably mounted on said transverse wall to prevent passage of said cannula through said wall.

25. A shielded hypodermic needle assembly as set forth in claim 24 wherein said tubular shield has a cap forming said transverse wall and said cover is of disc shape and is slidably mounted on said cap.

Signed and Sealed this

Twenty-fifth Day of October, 1994

*Attest:*

Bruce Lehman

BRUCE LEHMAN

*Attesting Officer*

*Commissioner of Patents and Trademarks*